United States Patent [19]

Watkinson

[11] Patent Number: 4,753,931
[45] Date of Patent: Jun. 28, 1988

[54] NEMATICIDAL TETRACHLOROETHYL PHOSPHOROTHIOATE

[75] Inventor: Ian A. Watkinson, Modesto, Calif.

[73] Assignee: E. I. Du Pont de Nemours and Company, Wilmington, Del.

[21] Appl. No.: 884,832

[22] Filed: Jul. 14, 1986

[51] Int. Cl.⁴ .............................................. A01N 57/10
[52] U.S. Cl. .................................................... 514/144
[58] Field of Search ........................................ 514/144

[56] References Cited

U.S. PATENT DOCUMENTS 3,027,296  3/1962  Whetstone ......................... 514/141

FOREIGN PATENT DOCUMENTS 160344  11/1985  European Pat. Off. .
107581  8/1974   German Democratic Rep. .
123096  11/1976  German Democratic Rep. .

*Primary Examiner*—Allen J. Robinson

[57] ABSTRACT

A method for controlling nematodes at a locus which comprises applying to the nematodes or the locus a nematicidally-effective amount of O,O-diethyl O-(1,2,2,2-tetrachloroethyl)phosphorothioate.

14 Claims, No Drawings

NEMATICIDAL TETRACHLOROETHYL PHOSPHOROTHIOATE

BACKGROUND OF THE INVENTION

1. Field of the Invention The present invention relates to a method of controlling nematodes with 0,0-diethyl 0-(1,2,2,2-tetrachloroethyl) phosphorothioate.

2. Description of the Prior Art U.S. Pat. No. 3,027,296 describes a number of halogenated phosphorus esters, including 0,0-diethyl 0-(1,2,2,2-tetrachloroethyl) phosphorothioate at columns 7 and 8, as insecticides. This patent shows testing of certain of the halogenated phosphorus esters for insecticidal activity on houseflies, two-spotted mites and pea aphids. None of these tests involved application and use of these halogenated phosphorus compounds as soil insecticides in the soil habitat of insects or their larvae. The patent suggests that the compounds have systemic insecticidal activity when applied to the soil in the vicinity of growing plants or directly to the plants.

East German Pat. No. 123,096 also discloses various polyhaloalkyl phosphate esters, including 0,0-dimethyl and 0,0-diethyl 0-(1,2,2,2-tetrachloroethyl) phosphorothioate as compounds 41 and 42, and broadly their use as insecticides. Similar disclosures are found in East German Pat. No. 107,581.

None of these patents disclose the control of nematodes which feed on growing plants that is afforded by the tetrachloroethyl phosphorothioate of the present invention. Indeed, nematicidal activity is not common to all insecticides or even all soil insecticides because of the different characteristics of the unsegmented roundworms that comprise the class Nematoda as compared to the creatures of the class Insecta.

SUMMARY OF THE INVENTION

The present invention is directed to a method of controlling nematodes at a locus which comprises applying to the nematodes or the locus a nematicidally effective amount of 0,0-diethyl 0-(1,2,2,2-tetrachloroethyl) phosphorothioate.

The material of the invention is useful for controlling a variety of Nematoda that are damaging to growing plants, including viable seeds thereof. The material of the invention is well suited for the control of Nematoda species, for example, (a) cyst forming nematodes that form cysts covering their eggs, (b) endoparasitic nematodes that enter the root tissue or permanently attach themselves to it, (c) ectoparasitic nematodes that feed on the root surface and normally do not enter the root tissue, and (d) above ground feeding nematodes that feed within plant tissue above ground, including species of the genera Meloidogyne, Heterodera, Aphelenchoides, Longidorus, Xiphinema, Criconemoides, Rotylenchulus, Trichodorus, Tylenchorhynchus, Hoplolaimus, Helicotylenchus, Pratylenchus, Radopholus, Ditylenchus, Tylenchulus, Belonolaimus, and the like, including such species as *Meloidogyne incognita,* southern root knot nematode, *Meloidogyne incognita* var. acrita, *Meloidogyne graminicola,* sorghum root knot nematode, *Aphelenchoides besseyi,* rice white-tip nematode, *Heterodera sacchari,* sugar cane cyst nematode, *Heterodera glycines,* soybean cyst nematode, *Heterodera cruciferae,* cabbage root nematode, *Heterodera schachtii,* sugar beet nenatode, *Heterodera tabacum,* tobacco cyst nematode, *Tylenchorhynchus claytoni,* stunt nematode, *Pratylenchus penetrans,* lesion nematode, *Pratylenchus zeae,* corn nematode, *Radopholus similis,* burrowing nematode, *Ditylenchus dispsaci,* teasel nematode, *Tylenchulus semipentrans,* citrus nematode, *Helicotylenchus dihystera,* a spiral nematode, *Holpolaimus galeatus* a lance nematode, *Belonolaimus longicaudatus* sting nematode, or the like.

0,0-Diethyl 0-(1,2,2,2-tetrachloroethyl) phosphorothioate has unexpectedly high activity against nematodes, which feed on growing plants, by virtue of its application to the nematodes or a locus such as the plants, the soil habitat of the plants and the like and its persistent effectiveness over an extended period of time. Since the various kinds of soil-inhibiting nematodes to be controlled in the various life stages do not manifest a problem or potential problem in the same way or at the same period of time, it is especially difficult to effectively control these nematodes by one application of a single chemical agent before the plants, which might be damaged by the nematodes, have even emerged. For example, (a) throughout the growing season in which nematode species infest the ground and attack the seed, the roots or even above ground plant parts, (b) in seedling corn where usually two to three weeks following corn planting nematode species infest the ground, near, yet beneath its surface, and damage the seedling at ground level, or (c) five to seven weeks after corn planting, and nematodes species infest the ground, up to six inches below the surface, damaging by feeding the roots of the corn.

To control the nematodes by application before the plant has emerged requires a material that is effective for an extended period of time. Thus, the material to control nematodes, which usually inhabit the soil or inside the plant and feed upon plants, should have persistence and, preferably, ovicidal activity as well as larvicidal activity.

The compound of the invention is generally not applied full technical strength but is typically applied as formulations which may be applied as such or further diluted for application. Typical formulations include compositions of the active ingredient in combination with one or more agriculturally acceptable adjuvants, carriers or extenders, preferably with a surface active agent, and optionally with other active ingredients. Suitable formulations include granules, powders, or liquids, the choice varying with the type of nematode pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application.

With due consideration to these factors the active ingredient of a typical formulation may, for example, be suitably present at a concentration of about 0.01% up to about 95%, preferably 0.1% up to 90% of the formulation, agriculturally acceptable carriers, diluents, adjuvants, and other suitable active ingredients comprising the balance of the formulation. Compatible surface active agents, if employed in a formulation, may be present at various concentrations, suitably in the range of 1 to 30% by weight of the formulation.

The formulation may be used as such or diluted to a desired use dilution with a diluent or liquid carrier suitable for facilitating dispersion of the active ingredients. A suitable concentration of the active ingredient in the use dilution may be in the range of 0.005% to 10%, more preferably 0.01% to about 10%, by weight.

The material of the invention can also be conveniently formulated for use as slow release compositions, granules, dusts or wettable powders containing a solid diluent, impregnated with the material of the invention. Such solid formulations usually contain from about 1 to 50% by weight of the material of the invention.

The material of the invention can be applied as a band, furrow or side dress, either incorporated or not. More effective control will result when the formulation is physically lightly mixed with the topsoil. The mixing is concurrent with, preceded or followed by planting seed which germinate into plants or on transplanting. The material of the invention can also be applied to the soil or plants as a liquid drench or emulsifiable concentrate or the like that is as a solution or dispersion of the material of the invention in a non-phytotoxic solvent or liquid diluent, suitably water or other agriculturally acceptable carrier. Such drenches can be prepared, for example by diluting with water a concentrate containing the materials of the invention, an emulsifying agent, and preferably an organic solvent such as toluene.

Many variations of spraying, dusting, and controlled or slow release compositions of a type known in the art may be used by substituting or adding the nematicidal compound of this invention into the compositions known or apparent to the art.

The nematicidal compound of this invention may be formulated and applied with other compatible active agents including nematicides, insecticides, acaricides, fungicides, plant growth regulators, herbicides, fertilizers, and the like.

In applying the compound of the invention, whether alone or with other agricultural chemicals, an effective nematicidal amount of the active ingredient must be applied. While the application rate will vary widely depending on the choice of compound, formulation, mode of application, plant species being protected, planting density, and other like factors, the material of the invention is suitably applied to the soil at a rate of from about 0.01 to about 11 kg/ha. Good control of soil inhabiting insects is obtained at rates of from about 0.1 to about 5 kg/ha, and especially from about 0.5 to about 4 kg/ha.

The 0,0-diethyl 0-(1,2,2,2-tetrachloroethyl) phosphorothioate used in the present invention can be prepared by various conventional methods of preparing phosphorus thio esters. In one such method chloral is treated with phosphorus pentachloride to give $CCl_3CHClOPCl_4$, which is treated with hydrogen sulfide to give the intermediate $CCl_3CHClOP(S)Cl_2$. This dichloridate is treated with ethanol to give the desired ester of the present invention. For this reaction with ethanol, an inert solvent can be present, but the reaction proceeds satisfactorily in the absence of a solvent. This reaction is preferably conducted at less than ambient temperatures by use of a cooling system, such as an ice bath. The addition of a conventional buffering agent, such as an alkali metal bicarbonate, is desirable. The reaction proceeds to completion after several hours or days. The resulting product mixture is diluted with an inert solvent, such as methylene chloride, washed, filtered and stripped of solvent. The crude product can be purified by one or more of the conventional methods of distillation, chromatography and extraction using inert solvents.

ILLUSTRATIVE EMBODIMENTS

The invention is illustrated by the following embodiments which describe the preparation of the compound of the invention and its use to control nematodes.

Embodiment 1

0,0-Diethyl 0-(1,2,2,2-tetrachloroethyl) phosphorothioate

To 31.6 of phosphorus pentachloride in 100 ml of carbon tetrachloride at 35° C. was added dropwise over ½ hour a mixture of 0.1 ml of acetonitrile and 9.8 ml of chloral. The reaction mixture was maintained at 34°–35° C. overnight, filtered, and the filtrate was cooled with ice. Hydrogen sulfide was bubbled through the cooled filtrate in an amount of 13.7 g over 3 hours. The reaction mixture was allowed to warm for a short time and the solvent was evaporated to leave 31.4 g of a yellow liquid, which was distilled in a kugelrohr at 60°–70° C. (0.1 mm) to give 10.3 g of yellow liquid mixed with some black solid. This material was vacuum chromatographed using hexane to give 9.1 g of 0-(1,2,2,2-tetrachloroethyl) phosphorothiodichloridate.

To 3.2 g of 0-(1,2,2,2-tetrachloroethyl) phosphorothiodichloridate was added 25 ml of ethanol. The reaction mixture was cooled for 45 minutes with ice and then an excess of sodium bicarbonate was added. After 3 days, the mixture was diluted with methylene chloride and washed with water. The separated organic phase was dried, evaporated and kugelrohr distilled at 75°–85° C. (0.05 mm) to give 2.0 g of liquid, which was vacuum chromatographed using hexane to yield 1.4 g of the desired product as a colorless liquid.

Embodiment 2

Nematode Test

The compound of the invention, was tested as a nematicide, as follows:

Soil Drench Test

Test soil/plants: 2 to 3 plants of grain sorghum (*Sorghum bicolor*) 6–7 centimeters in height growing in 55 cubic centimeters of loam soil in 5 centimeter pots. The soil in each pot was drenched with 2 milliliters of a solution/suspension of 10 parts per million of the test compound in a solution of 5% acetone in water containing 0.05% Triton X-155, and allowed to equilibrate, 24 hours after the treatment, the soil was inoculated with 2 milliliters of water containing approximately 500 Stage 2 juvenile *Meloidogyne graminicola* nematodes. The treated pots were held in a glasshouse for two weeks, then the roots of the plants were washed clean and the effects of the nematodes were evaluated visually. The effectiveness of the test compound was expressed in terms of an A B C system wherein A =0–20% infestation, B=21–50%, C=51–100% infestation. A compound achieving an A rating in the primary screen was retested at lower concentrations to obtain a dosage control curve. Two replicates were used at each concentration. The results were analyzed and corrected to account for the level of knot formation in the untreated controls.

In the tests, the Compound of the invention was determined to have a mean $EC_{50}$ rating (concentration, ppm, in the test solution) of 1.2.

Foliar Spray Test

Pots containing *S. bicolor* plants described in the soil drench test protocol were used. A layer of non-absorbent cotton wool was placed in each pot to protect the soil and lower part of each plant from spray contamination, and the plants were sprayed with a standard solution/suspension of the test compound, using an overhead track sprayer. The treated pots were left to dry for one hour, held in a glasshouse for 4 days, when they were inoculated with approximately 500 stage 2 juvenile *M. graminicola* nematodes, then held for two weeks and the effect of the test compound was evaluated as described in the soil drench test protocol.

The mean $EC_{50}$ dosage for the Compound of the invention was found to be 3 kilograms per hectare.

The compound of the invention also showed a steady increase in nematicidal activity with time, which was not found in the case of the commercial nematicide, oxamyl in comparative experiments.

What is claimed is:

1. A method for controlling nematodes at a locus which comprises applying to the nematodes a nematicidally effective amount of 0,0-diethyl 0-(1,2,2,2-tetrachloroethyl) phosphorothioate.

2. A method according to claim 1 wherein the nematodes are selected from the Helicotylenchus species.

3. A method according to claim 1 wherein the nematodes are selected from the Hoplolaimus species.

4. A method according to claim 1 wherein the nematodes are selected from the Meloidogyne species.

5. A method according to claim 4 wherein the nematodes are *Meloidogyne incognita, Meloidogyne incognita* var. acrita, or *Meloidogyne graminicola.*

6. A method according to claim 1 wherein the nematodes are selected from the Heterodera species.

7. A method according to claim 6 wherein the nematodes are *Heterodera cruciferae, Heterodera glycine, Heterodera schachtii, Heterodera saccari,* or *Heterodera tabacum.*

8. A method according to claim 1 wherein the nematodes are selected from the Pratylenchus species.

9. A method according to claim 1 wherein the nematodes are selected from the Belonolaimus species.

10. A method according to claim 9 wherein the nematodes are *Belonolaimus longicaudatus.*

11. A method according to claim 1 wherein the phosphorothioate is applied to the soil habitat of said nematodes by physically mixing with the topsoil of said soil.

12. A method according to claim 11 wherein the mixing is done concurrently with, preceded or followed by planting seeds which germinate into plants.

13. A method according to claim 1 wherein the phosphorothioate is applied in the amount of about 0.01 kg/ha to about 11 kg/ha.

14. A method according to claim 13 wherein the phosphorothioate is applied in the amount of about 0.1 to about 5 kg/ha.

* * * * *